United States Patent
Oard et al.

(12)

(10) Patent No.: US 10,834,885 B1
(45) Date of Patent: Nov. 17, 2020

(54) HYBRID RICE DESIGNATED 'LAH169'

(71) Applicant: Board of Supervisors of Louisiana State University and Agricultural and Mechanical College, Baton Rouge, LA (US)

(72) Inventors: James H. Oard, Crowley, LA (US); Steven D. Linscombe, Mountain Home, TX (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 16/453,295

(22) Filed: Jun. 26, 2019

Related U.S. Application Data

(60) Provisional application No. 62/694,049, filed on Jul. 5, 2018.

(51) Int. Cl.
*A01H 5/10* (2018.01)
*A01H 6/46* (2018.01)

(52) U.S. Cl.
CPC ............. *A01H 6/4636* (2018.05); *A01H 5/10* (2013.01)

(58) Field of Classification Search
None
See application file for complete search history.

(56) References Cited

U.S. PATENT DOCUMENTS 8,153,870 B2 * 4/2012 Re ............................ A01H 5/10
435/410

OTHER PUBLICATIONS

LSU Rice Research Station Annual Report 2008, p. 11.
LSU Rice Research Station Annual Report 2014, pp. 69-73, 264.
LSU Rice Research Station Annual Report 2015, pp. 5, 6, 8, 10, 13, 15, 17, 52, 58-60, 62, 149, 151, 153, 252.
LSU Rice Research Station Annual Report 2016, pp. 5, 6, 8, 10, 12, 14, 16, 18, 70, 79, 81.
LSU Rice Research Station Annual Report 2017, pp. 5, 6, 8, 10, 12, 15, 18, 21, 94, 95.
LSU Rice Research Station Annual Report 2018, pp. 116, 141-144, 400, 404.
Schultz, "LSU AgCenter releases new rice hybrid," press release (Mar. 21, 2018).

* cited by examiner

*Primary Examiner* — Medina A Ibrahim
(74) *Attorney, Agent, or Firm* — John H. Runnels

(57) ABSTRACT

A hybrid rice designated 'LAH169' is disclosed.

16 Claims, No Drawings

US 10,834,885 B1

HYBRID RICE DESIGNATED 'LAH169'

The benefit of the filing date of U.S. provisional application 62/694,049, filed Jul. 5, 2018, is claimed under 35 U.S.C. § 119(e).

TECHNICAL FIELD

This invention pertains to the hybrid rice designated 'LAH169.'

BACKGROUND ART

Rice is an ancient agricultural crop, and remains one of the world's principal food crops. There are two cultivated species of rice: *Oryza sativa* L., the Asian rice, and *O. glaberrima* Steud., the African rice. *Oryza sativa* L. constitutes virtually all of the world's cultivated rice and is the species grown in the United States. The three major rice-producing regions in the United States are the Mississippi Delta (Arkansas, Mississippi, northeast Louisiana, southeast Missouri), the Gulf Coast (southwest Louisiana, southeast Texas); and the Central Valley of California. See generally U.S. Pat. No. 6,911,589.

Rice is a semiaquatic crop that benefits from flooded soil conditions during part or all of the growing season. In the United States, rice is typically grown on flooded soil to optimize grain yields. Heavy clay soils or silt loam soils with hard pan layers about 30 cm below the surface are typical rice-producing soils, because they reduce water loss from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination comes from irrigation or rainfall. Another method of dry-seeding is to broadcast the seed by airplane into a flooded field, and then promptly drain the water from the field. For the dry-seeded system, when the plants have reached sufficient size (four- to five-leaf stage), a shallow permanent flood of water 5 to 16 cm deep is applied to the field for the remainder of the crop season. Some rice is grown in upland production systems, without flooding.

One method of water-seeding is to soak rice seed for 12 to 36 hours to initiate germination, and then to broadcast the seed by airplane into a flooded field. The seedlings emerge through a shallow flood, or the water may be drained from the field for a short time to enhance seedling establishment. A shallow flood is then maintained until the rice approaches maturity. For both the dry-seeded and water-seeded production systems, the fields are drained when the crop is mature, and the rice is harvested 2 to 3 weeks later with large combines.

In rice breeding programs, breeders typically use the same production systems that predominate in the region. Thus, a drill-seeded breeding nursery is typically used by breeders in a region where rice is drill-seeded, and a water-seeded nursery is typically used in regions where water-seeding prevails.

Rice in the United States is classified into three primary market types by grain size, shape, and endosperm composition: long-grain, medium-grain, and short-grain. Typical U.S. long-grain cultivars cook dry and fluffy when steamed or boiled, whereas medium- and short-grain cultivars cook moist and sticky. Long-grain cultivars have been traditionally grown in the southern states and generally receive higher market prices in the U.S.

Although specific breeding objectives vary somewhat in different regions, increasing yield is a primary objective in all programs. Grain yield depends, in part, on the number of panicles per unit area, the number of fertile florets per panicle, and grain weight per floret. Increases in any or all of these components may help improve yields. Heritable variation exists for each of these components, and breeders may directly or indirectly select for any of them.

There are numerous steps in the development of any novel, desirable plant germplasm. Plant breeding begins with the analysis and definition of problems and weaknesses of the current germplasm, the establishment of program goals, and the definition of specific breeding objectives. The next step is selection (or generation) of germplasm that possesses the desired traits to meet the program goals. A goal is often to combine in a single variety an improved combination of desirable traits from two or more ancestral germplasm lines. These traits may include such things as higher seed yield, resistance to disease or insects, better stems and roots, tolerance to low temperatures, and better agronomic characteristics or grain quality.

The choice of breeding and selection methods depends on the mode of plant reproduction, the heritability of the trait(s) being improved, and the type of seed that is used commercially (e.g., $F_1$ hybrid, versus pure line or inbred cultivars). For highly heritable traits, a choice of superior individual plants evaluated at a single location may sometimes be effective, while for traits with low or more complex heritability, selection is often based on mean values obtained from replicated evaluations of families of related plants. Selection methods include pedigree selection, modified pedigree selection, mass selection, recurrent selection, and combinations of these methods.

The complexity of inheritance influences the choice of breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively-inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines are thoroughly tested and compared to appropriate standards in environments representative of the commercial target area(s), typically for three or more years. The best lines become candidates for new commercial cultivars; those still deficient in a few traits may be used as parents to produce new populations for further selection.

These processes, which lead ultimately to marketing and distribution of new cultivars or hybrids, typically take 8 to 12 years from the time of the first cross; they may further rely on (and be delayed by) the development of improved breeding lines as precursors. Development of new cultivars and hybrids is a time-consuming process that requires precise forward planning and efficient use of resources. There are never assurances of a successful outcome.

A particularly difficult task is the identification of individual plants that are, indeed, genetically superior. A plant's phenotype results from a complex interaction of genetics and environment. One method for identifying a genetically superior plant is to observe its performance relative to other experimental plants and to a widely grown standard cultivar raised in an identical environment. Repeated observations from multiple locations can help provide a better estimate of genetic worth.

The goal of rice breeding is to develop new, unique, and superior rice cultivars and hybrids. The breeder initially selects and crosses two or more parental lines, followed by self-pollination and selection, producing many new genetic combinations. The breeder can generate billions of different genetic combinations via crossing, selfing, and mutation breeding. The traditional breeder has no direct control of genetics at the molecular level. Therefore, two traditional breeders working independently of one another will never develop the same line, or even very similar lines, with the same traits.

Each year, the plant breeder selects germplasm to advance to the next generation. This germplasm is grown under different geographical, climatic, and soil conditions. Further selections are then made, during and at the end of the growing season. The resulting cultivars (or hybrids) and their characteristics are inherently unpredictable. This is because the traditional breeder's selection occurs in unique environments, with no control at the molecular level, and with potentially billions of different possible genetic combinations being generated. A breeder cannot predict the final resulting line, except possibly in a very gross and generic fashion. Further, the same breeder may not produce the same cultivar twice, even starting with the same parental lines, using the same selection techniques. This uncontrollable variation results in substantial effort and expenditures in developing superior new rice cultivars (or hybrids); and makes each new cultivar (or hybrid) novel and unpredictable.

The selection of superior hybrid crosses is somewhat different. Hybrid seed is typically produced by manual crosses between selected male-fertile parents or by using genetic male sterility systems. These hybrids are typically selected for single gene traits that unambiguously indicate that a plant is indeed an $F_1$ hybrid with inherited traits from both presumptive parents, particularly the male parent (since rice normally self-fertilizes). Such traits might include, for example, a semi-dwarf plant type, pubescence, awns, or apiculus color. Additional data on parental lines, as well as the phenotype of the hybrid, influence the breeder's decision whether to continue with a particular hybrid cross or an analogous cross, using related parental lines.

Pedigree breeding and recurrent selection breeding methods are sometimes used to develop cultivars from breeding populations. These breeding methods combine desirable traits from two or more cultivars or other germplasm sources into breeding pools from which cultivars are developed by selfing and selection of desired phenotypes. The new cultivars are evaluated to determine commercial potential.

Pedigree breeding is often used to improve self-pollinating crops. Two parents possessing favorable, complementary traits are crossed to produce $F_1$ plants. An $F_2$ population is produced by selfing one or more $F_1$s. Selection of the superior individual plants may begin in the $F_2$ (or later) generation. Then, beginning in the $F_3$ (or other subsequent) generation, individual plants are selected. Replicated testing of panicle rows from the selected plants can begin in the $F_4$ (or other subsequent) generation, both to fix the desired traits and to improve the effectiveness of selection for traits that have low heritability. At an advanced stage of inbreeding (e.g., $F_6$ or $F_7$), the best lines or mixtures of phenotypically-similar lines are tested for potential release as new cultivars.

Mass and recurrent selection methods can also be used to improve populations of either self- or cross-pollinating crops. A genetically variable population of heterozygous individuals is either identified or created by intercrossing several different parents. The best offspring plants are selected based on individual superiority, outstanding progeny, or excellent combining ability. The selected plants are intercrossed to produce a new population in which further cycles of selection are continued.

Backcross breeding is often used to transfer genes for a simply inherited, highly heritable trait into a desirable homozygous cultivar or inbred line, which is the recurrent parent. The source of the trait to be transferred is called the donor parent. The resulting plant should ideally have the attributes of the recurrent parent (e.g., cultivar) and the desired new trait transferred from the donor parent. After the initial cross, individuals possessing the desired donor phenotype (e.g., disease resistance, insect resistance, herbicide tolerance) are selected and repeatedly crossed (backcrossed) to the recurrent parent.

The single-seed descent procedure in the strict sense refers to planting a segregating population, harvesting a sample of one seed per plant, and using the one-seed sample to plant the next generation. When the population has been advanced from the $F_2$ generation to the desired level of inbreeding, the several plants from which the lines are derived will each trace to different $F_2$ individuals. The number of plants in a population declines each generation, due to failure of some seeds to germinate or the failure of some plants to produce at least one seed. As a result, not all of the $F_2$ plants originally sampled in the population will be represented by progeny in subsequent generations.

In a multiple-seed procedure, the breeder harvests one or more seeds from each plant in a population and threshes them together to form a bulk. Part of the bulk is used to plant the next generation and part is held in reserve. The procedure has been referred to as modified single-seed descent or the pod-bulk technique. The multiple-seed procedure has been used to save labor at harvest. It is considerably faster to thresh panicles by machine than to remove one seed from each by hand as in the single-seed procedure. The multiple-seed procedure also makes it possible to plant the same number of seeds from a population for each generation of inbreeding. Enough seeds are harvested to compensate for plants that did not germinate or produce seed.

Other common and less-common breeding methods are known and used in the art. See, e.g., R. W. Allard, Principles of Plant Breeding (John Wiley and Sons, Inc., New York, N.Y., 1967); N. W. Simmonds, Principles of Crop Improvement (Longman, London, 1979); J. Sneep et al., Plant Breeding Perspectives (Pudoc, Wageningen, 1979); and W. R. Fehr, Principles of Cultivar Development: Theory and Technique (Macmillan Pub., New York, N.Y., 1987).

Proper testing should detect any major faults and establish the level of superiority or improvement over current cultivars. In addition to showing superior performance, there must be a demand for a new cultivar or hybrid; i.e., the new cultivar or hybrid should either be compatible with industry standards, or it should create a new market. The introduction of a new cultivar or hybrid may incur additional costs to the seed producer, the grower, processor, and consumer for such things as special advertising and marketing, altered seed and commercial production practices, and new product utilization. The testing that precedes the release of a new cultivar or hybrid should take into account research and development costs, in addition to technical superiority of the final cultivar or hybrid.

See Schultz, "LSU AgCenter releases new rice hybrid," press release (Mar. 21, 2018).

DISCLOSURE OF THE INVENTION

We have discovered a novel, high-yielding, early-maturing, nonaromatic, conventional long-grain rice hybrid designated 'LAH169.' The grain quality is excellent, with low levels of chalk, about 50% less chalk than is typical of other commercially available hybrids. 'LAH169' has typical southern long grain cereal chemistry quality and cooking characteristics. The main crop yield performance of 'LAH169' in twenty-five trials at five locations across three years in Louisiana was 94 percent of that of CLXL745, currently the most popular hybrid in Louisiana. In limited trials across two years, the combined main and ratoon yield of 'LAH169' was nearly the same as the combined main and ratoon yield of CLXL745.

In one embodiment, this invention allows for single-gene converted plants of 'LAH169.' The single transferred gene may be a dominant or recessive allele. Preferably, the single transferred gene confers a trait such as resistance to insects; resistance to one or more bacterial, fungal or viral diseases; male fertility or sterility; enhanced nutritional quality; enhanced processing qualities; or an additional source of herbicide resistance. The single gene may be a naturally occurring rice gene or a transgene introduced through genetic engineering techniques known in the art. The single gene also may be introduced through traditional backcrossing techniques or genetic transformation techniques known in the art.

In another embodiment, this invention provides regenerable cells for use in tissue culture of rice plant 'LAH169.' The tissue culture may allow for regeneration of plants having physiological and morphological characteristics of rice plant 'LAH169' and of regenerating plants having substantially the same genotype as rice plant 'LAH169.' Tissue culture techniques for rice are known in the art. The regenerable cells in tissue culture may be derived from sources such as embryos, protoplasts, meristematic cells, callus, pollen, leaves, anthers, root tips, flowers, seeds, panicles, or stems. In addition, the invention provides rice plants regenerated from such tissue cultures.

In some embodiments, the present invention provides a method for treating rice. The method comprises contacting 'LAH169' rice with an agronomically acceptable composition.

In one embodiment, the agronomically acceptable composition comprises at least one agronomically acceptable active ingredient.

In another embodiment, the agronomically acceptable active ingredient is selected from the group consisting of fungicides, insecticides, antibiotics, stress tolerance-enhancing compounds, growth promoters, herbicides, molluscicides, rodenticides, animal repellants, and combinations thereof.

Definitions

The following definitions apply throughout the specification and claims, unless context clearly indicates otherwise:

"Days to 50% heading." Average number of days from seeding to the day when 50% of all panicles are exerted at least partially through the leaf sheath. A measure of maturity.

"Grain Yield." Grain yield is measured in pounds per acre, at 12.0% moisture. Grain yield depends on a number of factors, including the number of panicles per unit area, the number of fertile florets per panicle, and grain weight per floret.

"Lodging Percent." Lodging is a subjectively measured rating, and is the percentage of plant stems leaning or fallen completely to the ground before harvest.

"Grain Length (L)." Length of a rice grain, or average length, measured in millimeters.

"Grain Width (W)." Width of a rice grain, or average width, measured in millimeters.

"Length/Width (L/W) Ratio." This ratio is determined by dividing the average length (L) by the average width (W).

"1000 Grain Wt." The weight of 1000 rice grains, measured in grams.

"Harvest Moisture." The percentage moisture in the grain when harvested.

"Plant Height." Plant height in centimeters, measured from soil surface to the tip of the extended panicle at harvest.

"Apparent Amylose Percent." The percentage of the endosperm starch of milled rice that is amylose. The apparent amylose percent is an important grain characteristic that affects cooking behavior. Standard long grains contain 20 to 23 percent amylose. Rexmont-type long grains contain 24 to 25 percent amylose. Short and medium grains contain 13 to 19 percent amylose. Waxy rice contains zero percent amylose. Amylose values, like most characteristics of rice, depend on the environment. "Apparent" refers to the procedure for determining amylose, which may also involve measuring some long chain amylopectin molecules that bind to some of the amylose molecules. These amylopectin molecules actually act similar to amylose in determining the relative hard or soft cooking characteristics.

"Alkali Spreading Value." An index that measures the extent of disintegration of the milled rice kernel when in contact with dilute alkali solution. It is an indicator of gelatinization temperature. Standard long grains have a 3 to 5 Alkali Spreading Value (intermediate gelatinization temperature).

"Peak Viscosity." The maximum viscosity attained during heating when a standardized, instrument-specific protocol is applied to a defined rice flour-water slurry.

"Trough Viscosity." The minimum viscosity after the peak, normally occurring when the sample starts to cool.

"Final Viscosity." Viscosity at the end of the test or cold paste.

"Breakdown." The peak viscosity minus the hot paste viscosity.

"Setback." Setback 1 is the final viscosity minus the trough viscosity. Setback 2 is the final viscosity minus the peak viscosity.

"RVA Viscosity." Viscosity, as measured by a Rapid Visco Analyzer, a widely used laboratory instrument to examine the paste viscosity or thickening ability of milled rice during the cooking process.

"Hot Paste Viscosity." Viscosity measure of rice flour/water slurry after being heated to 95° C. Lower values indicate softer and stickier cooking types of rice.

"Cool Paste Viscosity." Viscosity measure of rice flour/water slurry after being heated to 95° C. and uniformly cooled to 50° C. Values less than 200 indicate softer cooking types of rice.

"Allele." An allele is any of one or more alternate forms of the same gene. In a diploid cell or organism such as rice, the two alleles of a given gene occupy corresponding loci on a pair of homologous chromosomes.

"Backcrossing." Backcrossing is a process in which a breeder repeatedly crosses hybrid progeny back to one of the parents, for example, crossing a first generation hybrid F with one of the parental genotypes of the $F_1$ hybrid, and then crossing a second generation hybrid F$_2$ with the same parental genotype, and so forth.

"Essentially all the physiological and morphological characteristics." A plant having "essentially all the physiological and morphological characteristics" of a specified plant refers to a plant having the same general physiological and morphological characteristics, except for those characteristics that are derived from a particular converted gene.

"Quantitative Trait Loci (QTL)." Quantitative trait loci (QTL) refer to genetic loci that to some degree control numerically measurable traits, generally traits that are continuously distributed.

"Regeneration." Regeneration refers to the development of a plant from tissue culture.

"Single Gene Converted (Conversion)." Single gene converted (conversion) includes plants developed by backcrossing, wherein essentially all of the desired morphological and physiological characteristics of a parental variety are recovered, while also retaining a single gene that is transferred into the plants via crossing and backcrossing. The term can also refer to the introduction of a single gene through genetic engineering techniques known in the art.

MODES FOR CARRYING OUT THE INVENTION

'LAH169' is an early-maturing, non-aromatic, conventional (non-herbicide-tolerant) hybrid with excellent grain yield and quality. The hybrid was developed by the "two-line" breeding method at the H. Rouse Caffey Rice Research Station (RRS) in Crowley, La. 'LAH169' was developed from the cross 69S/RU0802189 at the RRS in 2011. 69S is an environmentally-sensitive male-sterile line obtained from the Guangxi Academy of Agricultural Sciences, Nanning, China. The pedigree of 69S is K06S/R669. Under summer field conditions at the RRS, 69S was pollen-sterile, but produced 30% to 50% seed set when grown in the winter rice nursery in Lajas, Puerto Rico, and also when grown in the RRS winter greenhouse. The fertile pollen parent RU0802189 (LM-1//CPRS/KBNT) is a conventional, long-grain elite inbred line developed at the RRS. 'LAH169' was first evaluated in 2015 in multi-location yield tests including the Commercial Advanced, Hybrid Advanced, and subsequently in 2016 in the Cooperative Uniform Regional Rice Nurseries (URN), under the experimental designation RU1602082.

'LAH169' averaged 42 inches in height in yield tests across Louisiana, which was the same height as commercial hybrid CLXL745, and 4-5 inches taller than CL111 and CL153. At 78 days to 50% heading, it is one day later than CLXL745, and 1-3 days earlier than CL111 and CL153.

The leaves, lemma and palea of 'LAH169' are pubescent. The spikelet and apiculus are straw-colored and the grain is non-aromatic.

'LAH169' has an average percent amylose content of 19.0, compared to 16.8 for CLXL745, 20.3 for CL111, and 20.0 for CL153. 'LAH169,' CLXL745, CL111, and CL153 have intermediate gelatinization temperatures.

Percent chalk of milled rice for 'LAH169' is 6.0, compared to 12.2 for CLXL745, 7.0 for CL111, and 0.40 for CL153.

'LAH169' is moderately resistant to rice blast, sheath blight, and bacterial panicle blight.

Variants observed and removed from increase fields of 69S, RU0802189, and 'LAH169' included any one or more of the following: taller, shorter, later, earlier, short-, medium- and intermediate-grain types, gold, purple, and black hull panicles. The total number of variants was fewer than 1 per 5000 plants.

The 'LAH169' rice plants have shown uniformity and stability (within limits imposed by environmental influence) for the traits described in the Hybrid Description Information below. The inbred parental lines have both been self-pollinated for a sufficient number of generations, with careful attention paid to uniformity of plant type, to ensure a degree of homozygosity and phenotypic stability sufficient for use in commercial hybrid seed production.

TABLE A

Development and Evaluation History of 'LAH169'
Pedigree - 69S/RU0802189

| Year | Test |
|---|---|
| 2011 | 69S/RU0802189 |
| 2012 | 12TC Observational |
| 2013 | 13TC Observational |
| 2014 | 14TC Observational |
| 2015 | 2015 CA |
| 2016 | 2016 URN, CA |
| 2017 | 2017 URN, CA |

Hybrid Description Information

Rice hybrid 'LAH169' was observed to possess the following morphological and other characteristics, based on averages of tests conducted at multiple locations over several growing seasons; data for other hybrids and varieties are shown for comparison:

TABLE B

| | Data Summary | | | | | |
|---|---|---|---|---|---|---|
| | Performance | | | | | |
| Trait | LAH169 | CLXL745 | CL111 | CL153 | Number of Tests | Reference |
| Grain Traits | | | | | | |
| Yield (lb/A) | 8802 | 9361 | 7579 | 8298 | 25 | Table 3 |
| % Whole Milled | 61.4 | 61.5 | 65.0 | 62.3 | 15 | Table 6 |
| % Total Milled | 74.0 | 74.0 | 73.0 | 72.0 | 15 | Table 9 |
| Length-Rough (mm) | 8.86 | 9.61 | 8.74 | 9.51 | 6 | Table 22 |
| Width-Rough (mm) | 2.75 | 2.71 | 2.61 | 2.42 | 6 | Table 22 |
| L/W Ratio-Rough | 3.22 | 3.54 | 3.35 | 3.92 | 6 | Table 22 |
| Thickness-Rough (mm) | 1.59 | 1.97 | 2.07 | 2.05 | 6 | Table 22 |
| Length-Brown (mm) | 6.98 | 7.44 | 6.68 | 7.26 | 6 | Table 22 |
| Width-Brown (mm) | 2.32 | 2.35 | 2.22 | 2.10 | 6 | Table 22 |

TABLE B-continued

Data Summary

| Trait | LAH169 | CLXL745 | CL111 | CL153 | Number of Tests | Reference |
|---|---|---|---|---|---|---|
| Performance | | | | | | |
| L/W Ratio-Brown | 3.01 | 3.17 | 3.01 | 3.45 | 6 | Table 22 |
| Thickness-Brown (mm) | 1.54 | 1.76 | 1.75 | 1.81 | 6 | Table 22 |
| Length-Milled (mm) | 6.85 | 7.13 | 6.36 | 6.95 | 6 | Table 22 |
| Width-Milled (mm) | 2.26 | 2.31 | 2.14 | 2.01 | 6 | Table 22 |
| L/W Ratio-Milled | 3.03 | 3.08 | 2.97 | 3.45 | 6 | Table 22 |
| Thickness-Milled (mm) | 1.34 | 1.71 | 1.66 | 1.71 | 6 | Table 22 |
| % Chalk - Milled | 6.00 | 12.20 | 7.00 | 0.40 | 1 | Table 22 |
| Plant Traits | | | | | | |
| Vigor | 5 | 4 | 4 | 4 | 16 | Table 12 |
| Height (in) | 42 | 42 | 37 | 36 | 28 | Table 15 |
| Days to 50% Heading | 78 | 77 | 79 | 81 | 26 | Table 18 |
| Disease Reaction | | | | | | |
| Blast | 1.2 | 1.3 | 2.7 | 1.2 | 8 | Table 19 |
| Bacterial Panicle Blight | 2.6 | 1.0 | 4.8 | 3.4 | 5 | Table 20 |
| Sheath Blight | 4.5 | 5.2 | 6.4 | 5.7 | 8 | Table 21 |

TABLE 1

Average main crop yields (lb/A) for LAH169, CLXL745, and CL111 for multiple trials and locations. (2015).

Abbreviations: URN or URRN = Uniform Regional Nursery; RRS = Louisiana State University Rice Research Station (Crowley, LA)
(Note: multiply lb/A by 1.121 to obtain kg/ha)

| TEST | LAH169 | CLXL745 | CL111 |
|---|---|---|---|
| CA - RRS | 8673 | 8474 | 8759 |
| CA - ACADIA | 7848 | 9344 | 7316 |
| CA - EVANGELINE | 7341 | 8807 | 5299 |
| CA - JEFF DAVIS | 9175 | 10138 | 6584 |
| CA - LAKE ARTHUR | 9097 | 10149 | 6764 |
| CA - ST LANDRY | 9074 | 9691 | 5922 |
| HYBRID ADV - RRS | 9495 (14998)† | 8480 (14702)† | 7836 (11480)† |
| HYBRID ADV - LA | 9090 | 10660 | 6710 |
| HYBRID ADV - SL | 9105 | 9010 | 9105 |
| 2015 Average | 8766 | 9417 | 7143 |

†First number is main crop yield at RRS. Number in parentheses is main + ratoon yield.

TABLE 2

Average main crop yields (lb/A) for LAH169, CLXL745, CL111, and CL153 for multiple trials and locations. (2016).

| TEST | LAH169 | CLXL745 | CL111 | CL153 |
|---|---|---|---|---|
| URN - LOUISIANA | 9652 | nd | 8797 | 9388 |
| URN - ARKANSAS | 9892 | nd | 8527 | 6829 |
| URN - MISSISSIPPI | 9797 | nd | 9767 | 10187 |
| CA - RRS | 9913 (13208)† | 10516 (13514) | 7830 (10907) | 8834 (10984) |
| CA - ACADIA | 7710 | 10179 | 6610 | 7410 |
| CA - EVANGELINE | 8850 | 9871 | 5547 | 7271 |
| CA - JEFF DAVIS | 9026 | 10209 | 7233 | 7827 |
| CA - LAKE ARTHUR | 7479 | 7979 | 6418 | 7451 |
| 2016 Average | 9040 | 9751 | 7591 | 8483 |

†First number is main crop yield at RRS. Number in parentheses is main + ratoon yield.
nd = no data collected at this location.

TABLE 3

Average main crop yields (lb/A) for LAH169, CLXL745, CL111, and CL153 for multiple trials and locations (2017).

| TEST | LAH169 | CLXL745 | CL111 | CL153 |
|---|---|---|---|---|
| URN - LOUISIANA | 8271 | nd | 7000 | 7245 |
| URN - ARKANSAS | 11581 | nd | 8527 | 9497 |
| URN - MISSISSIPPI | 10299 | nd | 9767 | 10187 |
| CA - RRS | 8269 | 9059 | 7830 | 8523 |
| CA - ACADIA | 7208 | 9772 | 6610 | 7410 |
| CA - EVANGELINE | 6796 | 7534 | 5547 | 7271 |
| CA - JEFF DAVIS | 7725 | 7985 | 7233 | 7827 |
| CA - ST. LANDRY | 10408 | 10507 | 5096 | 7006 |
| 2017 Average | 8820 | 8971 | 7201 | 8113 |
| 2015-2017 Grand Average | 8802 | 9361 | 7579 | 8298 |

TABLE 4

Whole-grain milled rice yield (%) for LAH169, CLXL745, CL111, and CL153, CA trials at RRS, Acadia, and Jeff Davis locations (2015).

| TEST | LAH169 | CLXL745 | CL111 | CL153 |
|---|---|---|---|---|
| CA - RRS | 61.0 | 63.5 | 68.2 | 69.4 |
| CA - ACADIA | 67.9 | 66.3 | 64.8 | 71.6 |
| CA - JEFF DAVIS | 71.3 | 69.4 | 73.3 | 51.1 |
| 2015 Average | 66.7 | 66.4 | 68.8 | 64.1 |

TABLE 5

Whole-grain milled rice yield (%) for LAH169, CLXL745, CL111, and CL153 at multiple tests and locations (2016).

| TEST | LAH169 | CLXL745 | CL111 | CL153 |
|---|---|---|---|---|
| URN - LOUISIANA | 55.0 | nd | 59.5 | 55.4 |
| URN - ARKANSAS | 59.4 | nd | 62.5 | 54.3 |
| URN - MISSISSIPPI | 63.1 | nd | 65.5 | 65.6 |
| CA - RRS | 63.8 | 62.7 | 68.7 | 65.6 |
| CA - EVANGELINE | 63.7 | 65.4 | 66.7 | 67.9 |
| CA - LAKE ARTHUR | 54.7 | 61.3 | 60.7 | 62.1 |
| 2016 Average | 60.0 | 63.1 | 63.9 | 61.8 |

TABLE 6

Whole-grain milled rice yield (%) for LAH169, CLXL745, CL111, and CL153 at multiple tests and locations (2017).

| TEST | LAH169 | CLXL745 | CL111 | CL153 |
|---|---|---|---|---|
| URN - LOUISIANA | 55.0 | nd | 59.0 | 55.7 |
| URN - ARKANSAS | 55.5 | nd | 61.3 | 62.0 |
| URN - MISSISSIPPI | 63.1 | nd | 65.6 | 65.6 |
| CA - RRS | 57.0 | 51.7 | 61.6 | 53.2 |
| CA - ACADIA | 55.0 | 54.1 | 65.7 | 66.3 |
| CA - LAKE ARTHUR | 59.0 | 58.8 | 60.0 | 63.6 |
| 2017 Average | 57.4 | 54.9 | 62.2 | 61.1 |
| 2015-2017 Grand Average | 61.4 | 61.5 | 65.0 | 62.3 |

TABLE 7

Total-grain milled rice yield (%) for LAH169, CLXL745, and CL111 at RRS, Acadia, and Jeff Davis locations (2015).

| TEST | LAH169 | CLXL745 | CL111 |
|---|---|---|---|
| CA - RRS | 76 | 74 | 74 |
| CA - ACADIA | 78 | 79 | 79 |
| CA - JEFF DAVIS | 78 | 78 | 79 |
| 2015 Average | 75 | 77 | 75 |

TABLE 8

Total-grain milled rice yield (%) for LAH169, CLXL745, CL111, and CL153 at multiple tests and locations (2016).

| TEST | LAH169 | CLXL745 | CL111 | CL153 |
|---|---|---|---|---|
| URN - LOUISIANA | 75 | nd | 71 | 71 |
| URN - ARKANSAS | 71 | nd | 70 | 65 |
| URN - MISSISSIPPI | 72 | nd | 71 | 71 |
| CA - RRS | 74 | 71 | 74 | 71 |
| CA - EVANGELINE | 74 | 76 | 74 | 74 |
| CA - LAKE ARTHUR | 70 | 73 | 71 | 71 |
| 2016 Average | 73 | 73 | 72 | 70 |

TABLE 9

Total-grain milled rice yield (%) for LAH169, CLXL745, CL111, and CL153 at multiple tests and locations (2017).

| TEST | LAH169 | CLXL745 | CL111 | CL153 |
|---|---|---|---|---|
| URN - LOUISIANA | 74 | nd | 74 | 74 |
| URN - ARKANSAS | 68 | nd | 70 | 70 |
| URN - MISSISSIPPI | 72 | nd | 71 | 71 |
| CA - RRS | 76 | 76 | 75 | 73 |
| CA - ACADIA | 72 | 69 | 70 | 74 |
| CA - LAKE ARTHUR | 73 | 72 | 69 | 73 |
| 2017 Average | 72 | 73 | 71 | 72 |
| 2015-2017 Average | 74 | 74 | 73 | 72 |

TABLE 10

Seedling vigor for LAH169, CLXL745, and CL111 for multiple trials and locations (2015).

| TEST | LAH169 | CLXL745 | CL111 |
|---|---|---|---|
| CA - RRS | 4 | 3 | 4 |
| CA - ACADIA | 5 | 3 | 3 |
| CA - EVANGELINE | 6 | 6 | 4 |
| CA - JEFF DAVIS | 5 | 3 | 3 |
| CA - LAKE ARTHUR | 4 | 3 | 3 |
| 2015 AVERAGE | 5 | 4 | 3 |

TABLE 11

Seedling vigor for LAH169, CLXL745, CL111 and CL153 for multiple trials and locations (2016).

| TEST | LAH169 | CLXL745 | CL111 | CL153 |
|---|---|---|---|---|
| CA - RRS | 3 | 3 | 3 | 4 |
| CA - ACADIA | 6 | 5 | 4 | 5 |
| CA - EVANGELINE | 6 | 6 | 4 | 5 |
| CA - JEFF DAVIS | 6 | 6 | 5 | 5 |
| CA - LAKE ARTHUR | 6 | 4 | 4 | 5 |
| 2016 Average | 5 | 5 | 4 | 5 |

TABLE 12

Seedling vigor for LAH169, CLXL745, CL111 and CL153 for multiple trials and locations (2017).

| TEST | LAH169 | CLXL745 | CL111 | CL153 |
|---|---|---|---|---|
| CA - RRS | 4 | 5 | 4 | 3 |
| CA - ACADIA | 6 | 3 | 4 | 4 |
| CA - EVANGELINE | 5 | 3 | 4 | 3 |
| CA - JEFF DAVIS | 5 | 2 | 7 | 5 |
| CA - LAKE ARTHUR | 7 | 3 | 6 | 5 |
| CA - ST. JOE | 6 | 4 | 5 | 4 |
| 2017 Average | 5 | 3 | 5 | 4 |
| 2015-2017 Grand Average | 5 | 4 | 4 | 4 |

TABLE 13

Average plant height (in) for LAH169, CLXL745, and CL111 at multiple trials and locations (2015).

| TEST | LAH169 | CLXL745 | CL111 |
|---|---|---|---|
| URN - LOUISIANA | 45 | nd | 38 |
| URN - ARKANSAS | 48 | nd | 44 |
| URN - MISSISSIPPI | 45 | nd | 42 |
| URN - TEXAS | 40 | nd | 30 |
| CA - RRS | 42 | 45 | 40 |
| CA - ACADIA | 35 | 37 | 38 |
| CA - EVANGELINE | 42 | 42 | 35 |
| CA - JEFF DAVIS | 43 | 41 | 34 |
| CA - LAKE ARTHUR | 43 | 44 | 38 |
| CA - ST LANDRY | 38 | 34 | 30 |
| 2015 Average | 42 | 40 | 37 |

TABLE 14

Average plant height (in) for LAH169, CLXL745, CL111, and CL153 at multiple trials and locations (2016).

| TEST | LAH169 | CLXL745 | CL111 | CL153 |
|---|---|---|---|---|
| URN - LOUISIANA | 46 | nd | 38 | 37 |
| URN - ARKANSAS | 50 | nd | 45 | 44 |
| URN - MISSISSIPPI | 50 | nd | 46 | 44 |
| CA - RRS | 42 | 44 | 38 | 36 |
| CA - ACADIA | 48 | 47 | 39 | 39 |
| CA - EVANGELINE | 42 | 44 | 36 | 37 |
| CA - JEFF DAVIS | 42 | 46 | 38 | 37 |
| CA - LAKE ARTHUR | 42 | 43 | 30 | 35 |
| 2016 Average | 43 | 45 | 36 | 37 |

TABLE 15

Average plant height (in) for LAH169, CLXL745, CL111, and CL153 at multiple trials and locations (2017).

| TEST | LAH169 | CLXL745 | CL111 | CL153 |
|---|---|---|---|---|
| URN - LOUISIANA | 38 | nd | 33 | 31 |
| URN - ARKANSAS | 50 | nd | 39 | 40 |
| URN - MISSISSIPPI | 50 | nd | 45 | 44 |
| CA - RRS | 38 | 39 | 35 | 35 |
| CA - ACADIA | 33 | 38 | 35 | 33 |
| CA - EVANGELINE | 41 | 37 | 33 | 37 |
| CA - JEFF DAVIS | 38 | 41 | 36 | 33 |
| CA - LAKE ARTHUR | 43 | 39 | 33 | 34 |
| CA - ST JOE | 42 | 43 | 38 | 35 |
| CA - ST LANDRY | 43 | 43 | 39 | 39 |
| 2017 Average | 42 | 40 | 37 | 36 |
| 2015-2017 Grand Average | 42 | 42 | 37 | 36 |

TABLE 16

Average number of days to 50% heading for LAH169, CLXL745, and CL111 at multiple trials and locations (2015).

| TEST | LAH169 | CLXL745 | CL111 |
|---|---|---|---|
| URN - LOUISIANA | 83 | nd | 86 |
| URN - ARKANSAS | 92 | nd | 97 |
| URN - MISSISSIPPI | 78 | nd | 85 |
| URN - TEXAS | 75 | nd | 72 |
| CA - RRS | 90 | 80 | 84 |
| CA - ACADIA | 77 | 73 | 73 |
| CA - EVANGELINE | 69 | 68 | 63 |
| CA - JEFF DAVIS | 70 | 72 | 84 |
| CA - LAKE ARTHUR | 74 | 73 | 72 |
| 2015 Average | 79 | 73 | 79 |

TABLE 17

Average number of days to 50% heading for LAH169, CLXL745, CL111, and CL153 at multiple trials and locations (2016).

| TEST | LAH169 | CLXL745 | CL111 | CL153 |
|---|---|---|---|---|
| URN - LOUISIANA | 70 | nd | 75 | 78 |
| URN - ARKANSAS | 82 | nd | 85 | 87 |
| URN - MISSISSIPPI | 72 | nd | 73 | 77 |
| CA - RRS | 70 | 70 | 72 | 75 |
| CA - ACADIA | 72 | 74 | 72 | 79 |
| CA - EVANGELINE | 74 | 75 | 74 | 75 |
| CA - JEFF DAVIS | 79 | 79 | 81 | 84 |
| CA - LAKE ARTHUR | 77 | 78 | 75 | 84 |
| 2016 Average | 74 | 75 | 76 | 80 |

TABLE 18

Average number of days to 50% heading for LAH169, CLXL745, CL111, and CL153 at multiple trials and locations (2017).

| TEST | LAH169 | CLXL745 | CL111 | CL153 |
|---|---|---|---|---|
| URN - LOUISIANA | 78 | nd | 78 | 80 |
| URN - ARKANSAS | 76 | nd | 79 | 82 |
| URN - MISSISSIPPI | 72 | nd | 91 | 91 |
| CA - RRS | 83 | 83 | 81 | 81 |
| CA - ACADIA | 83 | 81 | 79 | 85 |
| CA - EVANGELINE | 90 | 76 | 83 | 90 |
| CA - JEFF DAVIS | 86 | 85 | 85 | 87 |
| CA - LAKE ARTHUR | 88 | 82 | 83 | 84 |
| CA - ST LANDRY | 83 | 84 | 78 | 89 |
| 2017 Average | 82 | 82 | 82 | 85 |
| 2014-2017 Grand Average | 78 | 77 | 79 | 81 |

TABLE 19

Reaction of LAH169, CLXL745, CL111, and CL153 to blast disease caused by *Pyricularia oryzae* (2015-2017).

| TEST | LAH169 | CLXL745 | CL111 | CL153 |
|---|---|---|---|---|
| 2015 | | | | |
| URRN - RRS | 2.0 | nd | 1.5 | nd |
| HYBRID ADVANCED - EV | 1.0 | 2.0 | 6.0 | nd |
| HYBRID ADVANCED - JD | 0.0 | 1.0 | 4.0 | nd |
| HYBRID ADVANCED - VP | 2.0 | 2.0 | 4.0 | nd |
| 2015 Average | 1.2 | 1.7 | 3.9 | nd |
| 2016 | | | | |
| URRN - RRS | 0.0 | nd | 1.8 | 0.5 |
| HYBRID ADVANCED - JD | 0.0 | 0.0 | 0.0 | nd |
| HYBRID ADVANCED - EV | 1.0 | 2.0 | 5.0 | nd |
| 2016 Average | 0.3 | 1.0 | 2.3 | 0.5 |
| 2017 | | | | |
| URRN - RRS | 2.0 | nd | 2.0 | 2.0 |
| 2017 Average | 2.0 | nd | 2.0 | 2.0 |
| 2015-2017 Grand Average | 1.2 | 1.3 | 2.7 | 1.2 |

* Using a scale of 0 = very resistant to 9 = very susceptible.

TABLE 20

Reaction of LAH169, CLXL745, CL111, and CL153 to bacterial panicle blight caused by *Burkholderia glumae* (2015-2017).

| TEST | LAH169 | CLXL745 | CL111 | CL153 |
|---|---|---|---|---|
| 2015 | | | | |
| URRN - RRS | 2.0 | nd | 5.5 | nd |
| HYBRID ADVANCED - EV | 1.0 | 1.0 | 1.0 | nd |
| 2015 Average | 1.5 | 1.0 | 3.2 | nd |
| 2016 | | | | |
| URN - RRS | 3.5 | nd | 5.2 | 2.9 |
| HYBRID ADVANCED - JD | 1.0 | 1.0 | 5.0 | nd |
| 2016 Average | 2.2 | 1.0 | 4.2 | 2.9 |
| 2017 | | | | |
| URN-RRS | 4.0 | nd | 7.0 | 4.0 |
| 2017 Average | 4.0 | nd | 7.0 | 4.0 |
| 2015-2017 Grand Average | 2.6 | 1.0 | 4.8 | 3.4 |

* Using a scale of 0 = very resistant to 9 = very susceptible.

TABLE 21

Reaction of LAH169, CLXL745, CL111, and CL153 to sheath blight caused by *Rhizoctonia solani* (2015-2017).

| TEST | LAH169 | CLXL745 | CL111 | CL153 |
|---|---|---|---|---|
| 2015 | | | | |
| URRN - RRS | 3.5 | nd | 6.3 | nd |
| CA - JD | 5.0 | 3.0 | 7.0 | nd |
| CA - VP | 1.0 | 1.0 | 7.0 | nd |
| 2015 Average | 3.2 | 2.0 | 6.8 | nd |
| 2016 | | | | |
| URN - RRS | 6.5 | nd | 5.5 | 4.8 |
| CA - JD | 3.0 | 3.0 | 5.0 | nd |
| 2016 Average | 4.7 | 3.0 | 5.2 | 4.8 |
| 2017 | | | | |
| CA - RRS | 7.0 | nd | 7.0 | 7.0 |
| CA - JD | 5.0 | 6.0 | 7.0 | 6.0 |
| CA - SL | 5.0 | 7.0 | 8.0 | 7.0 |

TABLE 21-continued

Reaction of LAH169, CLXL745, CL111, and CL153 to sheath blight caused by *Rhizoctonia solani* (2015-2017).

| TEST | LAH169 | CLXL745 | CL111 | CL153 |
|---|---|---|---|---|
| 2017 Average | 5.7 | 6.5 | 7.3 | 6.7 |
| 2015-2017 Grand Average | 4.5 | 5.2 | 6.4 | 5.7 |

\* Using a scale of 0 = very resistant to 9 = very susceptible.

TABLE 22

Rough, brown and milled grain dimensions, and % chalk of milled rice, LAH169, CLXL745, CL111, and CL153, RRS, 2017

| Hybrid/Variety | Type | Length mm | Width mm | L/W Ratio | Thickness mm | % Chalk |
|---|---|---|---|---|---|---|
| LAH169 | Rough | 8.86 | 2.75 | 3.22 | 1.59 | — |
|  | Brown | 6.98 | 2.32 | 3.01 | 1.54 | — |
|  | Milled | 6.85 | 2.26 | 3.03 | 1.34 | 6.0 |
| CLXL745 | Rough | 9.61 | 2.71 | 3.54 | 1.97 | — |
|  | Brown | 7.44 | 2.35 | 3.17 | 1.76 | — |
|  | Milled | 7.13 | 2.31 | 3.08 | 1.71 | 12.2 |
| CL111 | Rough | 8.74 | 2.61 | 3.35 | 2.07 | — |
|  | Brown | 6.68 | 2.22 | 3.01 | 1.75 | — |
|  | Milled | 6.36 | 2.14 | 2.97 | 1.66 | 7.0 |
| CL153 | Rough | 9.51 | 2.42 | 3.92 | 2.05 | — |
|  | Brown | 7.26 | 2.10 | 3.45 | 1.81 | — |
|  | Milled | 6.95 | 2.01 | 3.45 | 1.71 | 0.4 |

TABLE 23

Amylose content and gelatinization temperature of LAH169, CLXL745, CL111 and CL153, RRS, 2016

| Hybrid/Variety | Amylose (%) (Markers) | Amylose (%) (Laboratory) | Gelatinization Temperature |
|---|---|---|---|
| LAH169 | Intermediate/low | 19.0 | Intermediate |
| CLXL745 | nd | 16.8 | Intermediate |
| CL111 | Intermediate | 20.3 | Intermediate |
| CL153 | Intermediate | 20.0 | Intermediate |

The rice plants hereof can also optionally be transformed with herbicide tolerance traits known in the art, e.g., with mutant acetohydroxyacid synthase large subunit (AHASL) proteins, mutant ACCase proteins, mutant EPSPS proteins, or mutant glutamine synthetase proteins; or as a mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or cytochrome P450 (CYP450) protein having herbicide-degrading activity.

The rice plants hereof can also optionally be transformed or even "stacked" with other traits including, but not limited to, pesticidal traits such as Bt Cry and other proteins having pesticidal activity toward coleopteran, lepidopteran, nematode, or other pests; nutritional or nutraceutical traits such as modified oil content or oil profile traits, high protein or high amino acid concentration traits, and other trait types known in the art.

Furthermore, in another embodiment, rice plants are generated, e.g. by the use of recombinant DNA techniques, breeding, or otherwise by selection for desired traits, plants that are able to synthesize one or more proteins to improve their productivity, oil content, tolerance to drought, salinity or other growth-limiting environmental factors, or tolerance to arthropod, fungal, bacterial, or viral pests or pathogens of rice plants.

Furthermore, in other embodiments, rice plants are generated, e.g. by the use of recombinant DNA techniques, breeding, or otherwise by selection for desired traits to contain a modified amount of one or more substances or to contain one or more new substances, for example, to improve human or animal nutrition, e.g. health-promoting long-chain omega-3 fatty acids or unsaturated omega-9 fatty acids. (Cf. Nexera® canola, Dow Agro Sciences, Canada).

Furthermore, in some embodiments, rice plants are generated, e.g. by the use of recombinant DNA techniques, breeding, or otherwise by selection for desired traits to contain increased amounts of vitamins, minerals, or improved profiles of nutraceutical compounds.

In one embodiment, rice plants are produced by single-trait transformation of one or both of the parental lines so that the resulting new hybrid rice plants inherit the new trait and so that they new hybrid plants, relative to a wild-type rice plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate (glucobrassicin), or 1-methoxy-3-indolylmethyl-glucosinolate (neoglucobrassicin)); phenolics (e.g., flavonoids (e.g., quercetin, kaempferol), hydroxycinnamoyl derivatives (e.g., 1,2,2'-trisinapoylgentiobiose, 1,2-diferuloylgentiobiose, 1,2'-disinapoyl-2-feruloylgentiobiose, or 3-O-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, rice plants are produced so that the new rice plants, relative to a wild-type rice plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavins/tannins (such as the procyanidins comprising coumarin, proanthocyanidins, catechins, and anthocyanins); flavones; phytoestrogens such as coumestans; lignans; resveratrol; isoflavones e.g. genistein, daidzein, and glycitein; resorcyclic acid lactones; organosulfur compounds; phytosterols; terpenoids such as carnosol, rosmarinic acid, glycyrrhizin and saponins; chlorophyll; chlorphyllin, sugars, anthocyanins, and vanilla.

In other aspects, the present invention provides a product prepared from the rice plants of the invention, for example, brown rice (e.g., cargo rice), broken rice (e.g., chits, brewer's rice), polished rice (e.g., milled rice), rice hulls (e.g., husks, chaff), rice bran, rice pollards, rice mill feed, rice flour, rice oil, oiled rice bran, de-oiled rice bran, arrak, rice wine, poultry litter, and animal feed.

Further Embodiments of the Invention

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, pods, leaves, stems, roots, anthers and the like. Thus, another aspect of this invention is to provide for cells that, upon growth and differentiation, produce a rice plant having essentially all of the physiological and morphological characteristics of 'LAH169.'

Techniques for transforming with and expressing desired structural genes and cultured cells are known in the art. Also, as known in the art, rice may be transformed and regenerated such that whole plants containing and expressing desired genes under regulatory control are obtained. General descriptions of plant expression vectors and reporter genes and transformation protocols can be found, for example, in Gruber et al., "Vectors for Plant Transformation, in Methods in Plant Molecular Biology & Biotechnology" in Glich et al. (Eds. pp. 89-119, CRC Press, 1993). For example, expression vectors and gene cassettes with the GUS reporter are available from Clone Tech Laboratories, Inc. (Palo Alto, Calif.), and expression vectors and gene cassettes with luciferase reporter are available from Promega Corp. (Madison, Wis.). General methods of culturing plant tissues are provided, for example, by Maki et al., "Procedures for Introducing Foreign DNA into Plants" in Methods in Plant Molecular Biology & Biotechnology, Glich et al., (Eds. pp. 67-88 CRC Press, 1993); by Phillips et al., "Cell-Tissue Culture and In-Vitro Manipulation" in Corn & Corn Improvement, 3rd Edition; and by Sprague et al., (Eds. pp. 345-387) American Society of Agronomy Inc., 1988. Methods of introducing expression vectors into plant tissue include the direct infection or co-cultivation of plant cells with *Agrobacterium tumefaciens*, Horsch et al., *Science*, 227:1229 (1985). Descriptions of *Agrobacterium* vectors systems and methods for *Agrobacterium*-mediated gene transfer are provided by Gruber et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with biolistic device- or *Agrobacterium*-mediated transformation. Transformed plants obtained with the germplasm of 'LAH169' are intended to be within the scope of this invention.

The present invention also provides rice plants regenerated from a tissue culture of the 'LAH169' variety or hybrid plant. As is known in the art, tissue culture can be used for the in vitro regeneration of a rice plant. For example, see Chu, Q. R. et al. (1999) "Use of bridging parents with high anther culturability to improve plant regeneration and breeding value in rice," *Rice Biotechnology Quarterly*, 38:25-26; Chu, Q. R. et al., "A novel plant regeneration medium for rice anther culture of Southern U.S. crosses," *Rice Biotechnology Quarterly*, 35:15-16 (1998); Chu, Q. R. et al., "A novel basal medium for embryogenic callus induction of Southern US crosses," *Rice Biotechnology Quarterly*, 32:19-20 (1997); and Oono, K., "Broadening the Genetic Variability By Tissue Culture Methods," *Jap. J Breed.*, 33 (Supp. 2), 306-307 (1983). Thus, another aspect of this invention is to provide cells that, upon growth and differentiation, produce rice plants having all, or essentially all, of the physiological and morphological characteristics of 'LAH169.'

Unless context clearly indicates otherwise, references in the specification and claims to 'LAH169' should be understood also to include single gene conversions of 'LAH169' (or of one of the parental lines) with a gene encoding a trait such as, for example, male sterility, herbicide resistance, resistance for bacterial, fungal, or viral disease, insect resistance, male fertility, enhanced nutritional quality, industrial usage, yield stability and yield enhancement.

Duncan et al., *Planta*, 165:322-332 (1985) reflects that 97% of the plants cultured that produced callus were capable of plant regeneration. Subsequent experiments with both inbreds and hybrids produced 91% regenerable callus that produced plants. In a further study, Songstad et al., *Plant Cell Reports*, 7:262-265 (1988) reported several media additions that enhanced regenerability of callus of two inbred lines. Other published reports also indicate that "nontraditional" tissues are capable of producing somatic embryogenesis and plant regeneration. K. P. Rao et al., *Maize Genetics Cooperation Newsletter*, 60:64-65 (1986), refers to somatic embryogenesis from glume callus cultures and B. V. Conger et al., Plant *Cell Reports*, 6:345-347 (1987) reported somatic embryogenesis from the tissue cultures of corn leaf segments. These methods of obtaining plants are routinely used with a high rate of success.

Tissue culture of corn (maize) is described in European Patent Application No. 160,390. Corn tissue culture procedures, which may be adapted for use with rice, are also described in Green et al., "Plant Regeneration in Tissue Culture of Maize," *Maize for Biological Research* (Plant Molecular Biology Association, Charlottesville, Va., pp. 367-372, 1982) and in Duncan et al., "The Production of Callus Capable of Plant Regeneration from Immature Embryos of Numerous *Zea Mays* Genotypes," 165 Planta, 322:332 (1985). Thus, another aspect of this invention is to provide cells that, upon growth and differentiation, produce rice plants having all, or essentially all, of the physiological and morphological characteristics of hybrid rice line 'LAH169.' See T. P. Croughan et al., (Springer-Verlag, Berlin, 1991) Rice (*Oryza sativa*. L): Establishment of Callus Culture and the regeneration of Plants, in Biotechnology in Agriculture and Forestry (19-37).

With the advent of molecular biological techniques that allow the isolation and characterization of genes that encode specific protein products, it is now possible to routinely engineer plant genomes to incorporate and express foreign genes, or additional or modified versions of native, or endogenous, genes (perhaps driven by different promoters) in order to alter the traits of a plant in a specific manner. Such foreign, additional, and modified genes are herein referred to collectively as "transgenes." In recent years, several methods for producing transgenic plants have been developed, and the present invention, in particular embodiments, also relates to transformed versions of 'LAH169.'

An expression vector is constructed that will function in plant cells. Such a vector comprises a DNA coding sequence that is under the control of or is operatively linked to a regulatory element (e.g., a promoter). The expression vector may contain one or more such operably linked coding sequence/regulatory element combinations. The vector(s) may be in the form of a plasmid or virus, and can be used alone or in combination with other plasmids or viruses to provide transformed rice plants.

Expression Vectors

Expression vectors commonly include at least one genetic "marker," operably linked to a regulatory element (e.g., a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are known in the art, and include, for example, genes that code for enzymes that metabolically detoxify a selective chemical inhibitor such as an antibiotic or a herbicide, or genes that encode an altered target that is insensitive to such an inhibitor. Positive selection methods are also known in the art.

For example, a commonly used selectable marker gene for plant transformation is that for neomycin phosphotransferase II (nptII), isolated from transposon Tn5, whose expression confers resistance to kanamycin. See Fraley et al., Proc. Natl. Acad. Sci. U.S.A., 80:4803 (1983). Another commonly used selectable marker gene is the hygromycin phosphotransferase gene, which confers resistance to the antibiotic hygromycin. See Vanden Elzen et al., Plant Mol. Biol., 5:299 (1985).

Additional selectable marker genes of bacterial origin that confer resistance to one or more antibiotics include gentamycin acetyl transferase, streptomycin phosphotransferase, aminoglycoside-3'-adenyl transferase, and the bleomycin resistance determinant. Hayford et al., Plant Physiol., 86:1216 (1988), Jones et al., Mol. Gen. Genet., 210:86 (1987), Svab et al., Plant Mol. Biol., 14:197 (1990); Plant Mol. Biol., 7:171 (1986). Other selectable marker genes confer resistance to herbicides such as glyphosate, glufosinate, or broxynil. Comai et al., Nature, 317:741-744 (1985); Gordon-Kamm et al., Plant Cell, 2:603-618 (1990); and Stalker et al., Science, 242:419-423 (1988).

Selectable marker genes for plant transformation of non-bacterial origin include, for example, mouse dihydrofolate reductase, plant 5-enolpyruvylshikimate-3-phosphate synthase, and plant acetolactate synthase. Eichholtz et al., Somatic Cell Mol. Genet. 13:67 (1987); Shah et al., Science, 233:478 (1986); and Charest et al., Plant Cell Rep., 8:643 (1990).

Another class of marker genes for plant transformation employs screening of presumptively transformed plant cells, rather than selection for resistance to a toxic substance such as an antibiotic. These marker genes are particularly useful to quantify or visualize the spatial pattern of expression of a gene in specific tissues, and are frequently referred to as reporter genes because they may be fused to the target gene or regulatory sequence. Commonly used reporter genes include glucuronidase (GUS), galactosidase, luciferase, chloramphenicol, and acetyltransferase. See Jefferson, R. A., Plant Mol. Biol. Rep., 5:387 (1987); Teeri et al., EMBO J., 8:343 (1989); Koncz et al., Proc. Natl. Acad. Sci. U.S.A., 84:131 (1987); and DeBlock et al., EMBO J., 3:1681 (1984). Another approach to identifying relatively rare transformation events has been the use of a gene that encodes a dominant constitutive regulator of the Zea mays anthocyanin pigmentation pathway. Ludwig et al., Science, 247:449 (1990).

The Green Fluorescent Protein (GFP) gene has been used as a marker for gene expression in prokaryotic and eukaryotic cells. See Chalfie et al., Science, 263:802 (1994). GFP and mutants of GFP may be used as screenable markers.

Genes included in expression vectors are driven by a nucleotide sequence comprising a regulatory element, for example, a promoter. Many suitable promoters are known in the art, as are other regulatory elements that may be used either alone or in combination with promoters.

As used herein, "promoter" refers to a region of DNA upstream or downstream from the transcription initiation site, a region that is involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter primarily drives expression in certain cell types in one or more organs, for example, vascular cells in roots or leaves. An "inducible" promoter is a promoter that is under environmental control. Examples of environmental conditions that may induce transcription by inducible promoters include anaerobic conditions or the presence of light. Tissue-specific, tissue-preferred, cell type specific, and inducible promoters are examples of "non-constitutive" promoters. A "constitutive" promoter is a promoter that is generally active under most environmental conditions.

A. Inducible Promoters

An inducible promoter is operably linked to a gene for expression in rice. Optionally, the inducible promoter is operably linked to a nucleotide sequence encoding a signal sequence that is operably linked to a gene for expression in rice. With an inducible promoter the rate of transcription increases in response to an inducing agent.

Any suitable inducible promoter may be used in the present invention. See Ward et al., Plant Mol. Biol., 22:361-366 (1993). Examples include those from the ACEI system, which responds to copper, Meft et al., PNAS, 90:4567-4571 (1993); In2 gene from maize, which responds to benzene-sulfonamide herbicide safeners, Hershey et al., Mol. Gen Genetics, 227:229-237 (1991); Gatz et al., Mol. Gen. Genetics, 243:32-38 (1994); and Tet repressor from Tn10, Gatz, Mol. Gen. Genetics, 227:229-237 (1991). A preferred inducible promoter is one that responds to an inducing agent to which plants do not normally respond, for example, the inducible promoter from a steroid hormone gene, the transcriptional activity of which is induced by a glucocorticosteroid hormone. See Schena et al., Proc. Natl. Acad. Sci., U.S.A. 88:0421 (1991).

B. Constitutive Promoters

A constitutive promoter is operably linked to a gene for expression in rice, or the constitutive promoter is operably linked to a nucleotide sequence encoding a signal sequence that is operably linked to a gene for expression in rice.

Constitutive promoters may also be used in the instant invention. Examples include promoters from plant viruses such as the 35S promoter from cauliflower mosaic virus, Odell et al., Nature, 313:810-812 (1985), and the promoters from the rice actin gene, McElroy et al., Plant Cell, 2:163-171 (1990); ubiquitin, Christensen et al., Plant Mol. Biol., 12:619-632 (1989) and Christensen et al., Plant Mol. Biol. 18:675-689 (1992); pEMU, Last et al., Theor. Appl. Genet., 81:581-588 (1991); MAS, Velten et al., EMBO 1, 3:2723-2730 (1984); and maize H3 histone, Lepetit et al., Mol. Gen. Genetics, 231:276-285 (1992) and Atanassova et al., Plant Journal, 2 (3): 291-300 (1992). An ACCase or AHAS promoter, such as a rice ACCase or AHAS promoter, may be used as a constitutive promoter.

C. Tissue-Specific or Tissue-Preferred Promoters

A tissue-specific promoter is operably linked to a gene for expression in rice. Optionally, the tissue-specific promoter is operably linked to a nucleotide sequence encoding a signal sequence that is operably linked to a gene for expression in rice. Transformed plants produce the expression product of the transgene exclusively, or preferentially, in specific tissue(s).

Any tissue-specific or tissue-preferred promoter may be used in the instant invention. Examples of tissue-specific or tissue-preferred promoters include those from the phaseolin gene, Murai et al., Science, 23:476-482 (1983), and Sengupta-Gopalan et al., Proc. Natl. Acad. Sci. U.S.A., 82:3320-3324 (1985); a leaf-specific and light-induced promoter such as that from cab or rubisco, Simpson et al., EMBO J., 4(11):2723-2729 (1985) and Timko et al., Nature, 318:579-

582 (1985); an anther-specific promoter such as that from LAT52, Twell et al., *Mol. Gen. Genetics,* 217:240-245 (1989); a pollen-specific promoter such as that from Zm13, Guerrero et al., *Mol. Gen. Genetics,* 244:161-168 (1993); or a microspore-preferred promoter such as that from apg, Twell et al., *Sex. Plant Reprod.,* 6:217-224 (1993).

Signal Sequences for Targeting Proteins to Subcellular Compartments

Transport of protein or peptide molecules produced by transgenes to a subcellular compartment such as a chloroplast, vacuole, peroxisome, glyoxysome, cell wall, or mitochondrion, or for secretion into an apoplast, is accomplished by operably linking a nucleotide sequence encoding a signal sequence to the 5' or 3' end of a gene encoding the protein or peptide of interest. Targeting sequences at the 5' or 3' end of the structural gene may determine, during protein synthesis and processing, where the encoded protein is ultimately compartmentalized.

Many signal sequences are known in the art. See, for example, Becker et al., *Plant Mol. Biol.,* 20:49 (1992); Close, P. S., Master's Thesis, Iowa State University (1993); Knox, C. et al., "Structure and Organization of Two Divergent Alpha-Amylase Genes from Barley," *Plant Mol. Biol.,* 9:3-17 (1987); Lerner et al., *Plant Physiol.,* 91:124-129 (1989); Fontes et al., *Plant Cell,* 3:483-496 (1991); Matsuoka et al., *Proc. Natl. Acad. Sci.,* 88:834 (1991); Gould et al., *J. Cell. Biol.,* 108:1657 (1989); Creissen et al., *Plant J.,* 1, 2:129 (1991); Kalderon et al., "A short amino acid sequence able to specify nuclear location," *Cell,* 39:499-509 (1984); and Steifel et al., "Expression of a maize cell wall hydroxyproline-rich glycoprotein gene in early leaf and root vascular differentiation," *Plant Cell,* 2:785-793 (1990).

Foreign Protein Genes and Agronomic Genes

Agronomically significant genes that may be transformed into rice plants in accordance with the present invention include, for example, the following:

1. Genes that Confer Resistance to Pests or Disease:
    A. Plant disease resistance genes. Plant defenses are often activated by specific interaction between the product of a disease resistance gene (R) in the plant and the product of a corresponding avirulence (Avr) gene in the pathogen. A plant may be transformed with a cloned resistance gene to engineer plants that are resistant to specific pathogen strains. See, e.g., Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); and Mindrinos et al., *Cell* 78:1089 (1994) (*Arabidopsis* RSP2 gene for resistance to *Pseudomonas syringae*).
    B. A *Bacillus thuringiensis* protein, a derivative thereof, or a synthetic polypeptide modeled thereon. See, e.g., Geiser et al., Gene 48:109 (1986), disclosing the cloning and nucleotide sequence of a Bt-endotoxin gene. DNA molecules encoding endotoxin genes may be obtained from American Type Culture Collection, Manassas, Va., e.g., under ATCC Accession Nos. 40098, 67136, 31995, and 31998.
    C. A lectin. See, for example, Van Damme et al., *Plant Molec. Biol.* 24:25 (1994), disclosing the nucleotide sequences of several *Clivia miniata* mannose-binding lectin genes.
    D. A vitamin-binding protein such as avidin. See PCT Application US93/06487. This disclosure teaches the use of avidin and avidin homologues as larvicides against insect pests.
    E. An enzyme inhibitor, e.g., a protease or proteinase inhibitor or an amylase inhibitor. See, e.g., Abe et al., *J. Biol. Chem.* 262:16793 (1987) (nucleotide sequence of rice cysteine proteinase inhibitor); Huub et al., *Plant Molec. Biol.* 21:985 (1993) (nucleotide sequence of cDNA encoding tobacco proteinase inhibitor 1); and Sumitani et al., *Biosci. Biotech. Biochem.* 57:1243 (1993) (nucleotide sequence of *Streptomyces nitrosporeus*-amylase inhibitor).
    F. An insect-specific hormone or pheromone such as an ecdysteroid and juvenile hormone, a variant thereof, a mimetic based thereon, or an antagonist or agonist thereof. See, e.g., Hammock et al., *Nature,* 344:458 (1990), disclosing baculovirus expression of cloned juvenile hormone esterase, an inactivator of juvenile hormone.
    G. An insect-specific peptide or neuropeptide that, upon expression, disrupts the physiology of the affected pest. See, e.g., Regan, *J. Biol. Chem.* 269:9 (1994) (expression cloning yields DNA coding for insect diuretic hormone receptor); and Pratt et al., *Biochem. Biophys. Res. Comm.,* 163:1243 (1989) (an allostatin in *Diploptera puntata*). See also U.S. Pat. No. 5,266,317 to Tomalski et al., disclosing genes encoding insect-specific, paralytic neurotoxins.
    H. An insect-specific venom produced in nature by a snake, a wasp, etc. For example, see Pang et al., *Gene,* 116:165 (1992), concerning heterologous expression in plants of a gene coding for a scorpion insectotoxic peptide.
    I. An enzyme responsible for hyperaccumulation of a monoterpene, a sesquiterpene, a steroid, hydroxamic acid, a phenylpropanoid derivative or another nonprotein molecule with insecticidal activity.
    J. An enzyme involved in the modification, including post-translational modification, of a biologically active molecule; e.g., a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, or a glucanase, either natural or synthetic. See PCT Application WO 9302197 to Scott et al., which discloses the nucleotide sequence of a callase gene. DNA molecules that contain chitinase-encoding sequences can be obtained, for example, from the American Type Culture Collection under Accession Nos. 39637 and 67152. See also Kramer et al., *Insect Biochem. Molec. Biol.* 23:691 (1993), which discloses the nucleotide sequence of a cDNA encoding tobacco hookworm chitinase; and Kawalleck et al., *Plant Molec. Biol.,* 21:673 (1993), which discloses the nucleotide sequence of the parsley ubi4-2 polyubiquitin gene.
    K. A molecule that stimulates signal transduction. See, e.g., Botella et al., *Plant Molec. Biol.,* 24:757 (1994), which discloses nucleotide sequences for mung bean calmodulin cDNA clones; and Griess et al., *Plant Physiol.,* 104:1467 (1994), which discloses the nucleotide sequence of a maize calmodulin cDNA clone.
    L. An antimicrobial or amphipathic peptide. See PCT Application WO 9516776 (disclosing peptide derivatives of Tachyplesin that inhibit fungal plant pathogens); and PCT Application WO 9518855 (disclosing synthetic antimicrobial peptides that confer disease resistance).

M. A membrane permease, a channel former or a channel blocker. See, e.g., Jaynes et al., *Plant Sci.*, 89:43 (1993), which discloses heterologous expression of a cecropin lytic peptide analog to render transgenic tobacco plants resistant to *Pseudomonas solanacearum*.

N. A viral-invasive protein or a complex toxin derived therefrom. For example, the accumulation of viral coat proteins in transformed plant cells induces resistance to viral infection or disease development caused by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. See Beachy et al., *Ann. Rev. Phytopathol.*, 28:451 (1990).

O. An insect-specific antibody or an immunotoxin derived therefrom. Thus, an antibody targeted to a critical metabolic function in the insect gut inactivates an affected enzyme, killing the insect. See Taylor et al., Abstract #497, Seventh Int'l Symposium on Molecular Plant-Microbe Interactions (Edinburgh, Scotland, 1994) (enzymatic inactivation in transgenic tobacco via production of single-chain antibody fragments).

P. A virus-specific antibody. See, e.g., Tavladoraki et al., *Nature*, 366:469 (1993), showing protection of transgenic plants expressing recombinant antibody genes from virus attack.

Q. A developmental-arrest protein produced in nature by a pathogen or a parasite. For example, fungal endo-1, 4-D-polygalacturonases facilitate fungal colonization and plant nutrient release by solubilizing plant cell wall homo-1,4-D-galacturonase. See Lamb et al., *Bio/Technology*, 10:1436 (1992). The cloning and characterization of a gene that encodes a bean endopolygalacturonase-inhibiting protein is described by Toubart et al., *Plant J.*, 2:367 (1992).

R. A developmental-arrest protein produced in nature by a plant. For example, Logemann et al., *Bio/Technology*, 10:305 (1992) reported that transgenic plants expressing the barley ribosome-inactivating gene have an increased resistance to fungal disease.

2. Genes that Confer Resistance to a Herbicide, for Example:

A. A herbicide that inhibits the growing point or meristem, such as an imidazolinone or a sulfonylurea. Exemplary genes in this category code for mutant ALS and AHAS enzymes as described, for example, by Lee et al., *EMBO J.*, 7:1241 (1988); and Miki et al., *Theor. Appl. Genet.*, 80:449 (1990), respectively. See, additionally, U.S. Pat. Nos. 5,545,822; 5,736,629; 5,773, 703; 5,773,704; 5,952,553; 6,274,796; 6,943,280; 7,019,196; 7,345,221; 7,399,905; 7,495,153; 7,754, 947; 7,786,360; 8,841,525; 8,841,526; 8,946,528; 9,029,642; 9,090,904; and 9,220220. Resistance to AHAS-acting herbicides may be through a mechanism other than a resistant AHAS enzyme. See, e.g., U.S. Pat. No. 5,545,822.

B. Glyphosate: Resistance may be imparted by mutant 5-enolpyruvl-3-phosphikimate synthase (EPSP) and aroA genes. Other phosphono compounds such as glufosinate: Resistance may be imparted by phosphinothricin acetyl transferase, PAT and *Streptomyces hygroscopicus* phosphinothricin-acetyl transferase, bar, genes. Pyridinoxy or phenoxy propionic acids and cyclohexones: Resistance may be imparted by ACCase inhibitor-encoding genes. See, e.g., U.S. Pat. No. 4,940,835 to Shah et al., which discloses the nucleotide sequence of a form of EPSP that confers glyphosate resistance. A DNA molecule encoding a mutant aroA gene can be obtained under ATCC Accession Number 39256, and the nucleotide sequence of the mutant gene is disclosed in U.S. Pat. No. 4,769,061 to Comai. European Patent Application No. 0333033 to Kumada et al.; and U.S. Pat. No. 4,975,374 to Goodman et al., disclose nucleotide sequences of glutamine synthetase genes that confer resistance to herbicides such as L-phosphinothricin. The nucleotide sequence of a phosphinothricin-acetyltransferase gene is provided in European Application No. 0242246 to Leemans et al. and DeGreef et al., *Bio/Technology*, 7:61 (1989), describing the production of transgenic plants that express chimeric bar genes coding for phosphinothricin acetyl transferase activity. Examples of genes conferring resistance to phenoxy propionic acids and cyclohexones, such as sethoxydim and haloxyfop, are the Accl-S1, Accl-S2, and Accl-S3 genes described by Marshall et al., *Theor. Appl. Genet.*, 83:435 (1992).

C. A herbicide that inhibits photosynthesis, such as a triazine (psbA and gs+ genes) or a benzonitrile (nitrilase gene). Przibilla et al., *Plant Cell*, 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. 1, 285:173 (1992).

3. Genes that Confer or Contribute to a Value-Added Trait, Such as:

A. Modified fatty acid metabolism, for example, by transforming a plant with an antisense sequence to stearyl-ACP desaturase, to increase stearic acid content of the plant. See Knultzon et al., *Proc. Natl. Acad. Sci. U.S.A.* 89:2624 (1992).

B. Decreased Phytate Content

1) Introduction of a phytase-encoding gene would enhance breakdown of phytate, adding more free phosphate to the transformed plant. See, e.g., Van Hartingsveldt et al., *Gene*, 127:87 (1993), which discloses the nucleotide sequence of an *Aspergillus niger* phytase gene.

2) A gene may be introduced to reduce phytate content. For example, this may be accomplished by cloning, and then reintroducing DNA associated with an allele that is responsible for maize mutants characterized by low levels of phytic acid, or a homologous or analogous mutation in rice may be used. See Raboy et al., *Maydica*, 35:383 (1990).

C. Carbohydrate composition may be modified, for example, by transforming plants with a gene coding for an enzyme that alters the branching pattern of starch. See Shiroza et al., *J. Bacteol.*, 170:810 (1988) (nucleotide sequence of *Streptococcus* mutant fructosyltransferase gene); Steinmetz et al., *Mol. Gen. Genet.*, 20:220 (1985) (nucleotide sequence of *Bacillus subtilis* levansucrase gene); Pen et al., *Bio/Technology*, 10:292 (1992) (production of transgenic plants that express

*Bacillus lichenifonnis* amylase); Elliot et al., *Plant Molec. Biol.,* 21:515 (1993) (nucleotide sequences of tomato invertase genes); Søgaard et al., *J. Biol. Chem.,* 268:22480 (1993) (site-directed mutagenesis of barley amylase gene); and Fisher et al., *Plant Physiol.,* 102: 1045 (1993) (maize endosperm starch branching enzyme 11).

Methods for Rice Transformation

Numerous methods for plant transformation are known in the art, including both biological and physical transformation protocols. See, e.g., Miki, et al., "Procedures for Introducing Foreign DNA into Plants" in *Methods in Plant Molecular Biology and Biotechnology*; Glick B. R. and Thompson, J. E. (Eds.) (CRC Press, Inc., Boca Raton, 1993), pp. 67-88. In addition, expression vectors and in vitro culture methods for plant cell or tissue transformation and regeneration of plants are known in the art. See, e.g., Gruber et al., "Vectors for Plant Transformation" in *Methods in Plant Molecular Biology and Biotechnology*, Glick B. R. and Thompson, J. E. (Eds.) (CRC Press, Inc., Boca Raton, 1993), pp. 89-119.

A. *Agrobacterium*-Mediated Transformation

One method for introducing an expression vector into plants is based on the natural transformation system of *Agrobacterium*. See, e.g., Horsch et al., *Science,* 227:1229 (1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of plants. See, e.g., Kado, C. I., *Crit. Rev. Plant Sci.,* 10:1 (1991). Descriptions of *Agrobacterium* vector systems and methods for *Agrobacterium*-mediated gene transfer are provided by Gruber et al., supra; Miki et al., supra; and Moloney, et al., *Plant Cell Reports,* 8:238 (1989). See also U.S. Pat. No. 5,591,616.

B. Direct Gene Transfer

Despite the fact the host range for *Agrobacterium*-mediated transformation is broad, it is more difficult to transform some cereal crop species and gymnosperms via this mode of gene transfer, although success has been achieved in both rice and corn. See Hiei et al., *The Plant Journal,* 6:271-282 (1994); and U.S. Pat. No. 5,591,616. Other methods of plant transformation exist as alternatives to *Agrobacterium*-mediated transformation.

A generally applicable method of plant transformation is microprojectile-mediated (so-called "gene gun") transformation, in which DNA is carried on the surface of microprojectiles, typically 1 to 4 μm in diameter. The expression vector is introduced into plant tissues with a biolistic device that accelerates the microprojectiles to typical speeds of 300 to 600 m/s, sufficient to penetrate plant cell walls and membranes. Sanford et al., *Part. Sci. Technol.,* 5:27 (1987); Sanford, J. C., *Trends Biotech.,* 6:299 (1988); Klein et al., *Bio/Technology,* 6:559-563 (1988); Sanford, J. C., *Physiol Plant,* 7:206 (1990); and Klein et al., *Biotechnology,* 10:268 (1992). Various target tissues may be bombarded with DNA-coated microprojectiles to produce transgenic plants, including, for example, callus (Type I or Type II), immature embryos, and meristematic tissue.

Another method for physical delivery of DNA to plants is sonication of target cells. Zhang et al., *Bio/Technology,* 9:996 (1991). Alternatively, liposome or spheroplast fusion has been used to introduce expression vectors into plants. Deshayes et al., *EMBO J.,* 4:2731 (1985); and Christou et al., *Proc Natl. Acad. Sci. U.S.A.,* 84:3962 (1987). Direct uptake of DNA into protoplasts, using $CaCl_2$ precipitation, polyvinyl alcohol or poly-L-ornithine, has also been reported. Hain et al., *Mol. Gen. Genet.,* 199:161 (1985); and Draper et al., *Plant Cell Physiol.,* 23:451 (1982). Electroporation of protoplasts and whole cells and tissues has also been described. Donn et al., in Abstracts of VIIth International Congress on *Plant Cell* and Tissue Culture IAPTC, A2-38, p. 53 (1990); D'Halluin et al., *Plant Cell,* 4:1495-1505 (1992); and Spencer et al., *Plant Mol. Biol.,* 24:51-61 (1994).

Following transformation of rice target tissues, expression of a selectable marker gene allows preferential selection of transformed cells, tissues, or plants, using regeneration and selection methods known in the art.

These methods of transformation may be used for producing a transgenic inbred line. The transgenic inbred line may then be crossed with another inbred line (itself either transformed or non-transformed), to produce a new transgenic inbred line. Alternatively, a genetic trait that has been engineered into a particular rice line may be moved into another line using traditional crossing and backcrossing techniques. For example, backcrossing may be used to move an engineered trait from a public, non-elite inbred line into an elite inbred line, or from an inbred line containing a foreign gene in its genome into an inbred line or lines that do not contain that gene.

The term "inbred rice plant" should be understood also to include single gene conversions of an inbred line. Backcrossing methods can be used with the present invention to improve or introduce a characteristic into an inbred line, such as the parental lines of hybrid 'LAH169,' which then results in introducing the characteristic into the $F_1$ hybrid.

Many single gene traits have been identified that are not regularly selected for in the development of a new inbred line, but that may be improved by crossing and backcrossing. Single gene traits may or may not be transgenic. Examples of such traits include male sterility, waxy starch, herbicide resistance, resistance for bacterial or fungal or viral disease, insect resistance, male fertility, enhanced nutritional quality, yield stability, and yield enhancement. These genes are generally inherited through the nucleus. Known exceptions to the nuclear genes include some genes for male sterility that are inherited cytoplasmically, but that still act functionally as single gene traits. Several single gene traits are described in U.S. Pat. Nos. 5,777,196; 5,948,957; and 5,969,212.

DEPOSIT INFORMATION

A sample of seeds of the rice hybrid designated 'LAH169' was deposited with the American Type Culture Collection (ATCC), 10801 University Boulevard, Manassas, Va. 20110-2209 on Jul. 3, 2018, and was assigned ATCC Accession No. PTA-125153. This deposit was made under the Budapest Treaty. All restrictions on the availability to the public of the material deposited under ATCC Accession No. PTA-125153 will be irrevocably and without restriction removed upon the granting of a patent on the present application.

MISCELLANEOUS

The complete disclosures of all references cited in this specification are hereby incorporated by reference. In the event of an otherwise irreconcilable conflict, however, the present specification shall control.

What is claimed:

1. A rice plant designated 'LAH169,' a representative sample of seeds of said 'LAH169' rice having been deposited under ATCC Accession No. PTA-125153.

2. A rice seed of the rice plant of claim 1, wherein said seed comprises at least one cell of the rice plant designated 'LAH169'.

3. A composition comprising a product prepared from the rice plant of claim 1, wherein said product comprises at least one cell of the rice plant designated 'LAH169'.

4. A tissue culture of regenerable cells or protoplasts produced from the rice plant of claim 1.

5. The tissue culture of claim 4, wherein said regenerable cells or protoplasts are produced from a tissue selected from the group consisting of embryos, meristematic cells, pollen, leaves, anthers, roots, root tips, flowers, seeds, and stems.

6. A method for producing rice plants, said method comprising planting a plurality of rice seeds of the rice plant of claim 1, or a plurality of rice seeds capable of producing said rice plant, under conditions favorable for the growth of rice plants.

7. The method of claim 6, additionally comprising the step of producing rice seed from the resulting rice plants.

8. A method of producing an insect-resistant rice plant, said method comprising transforming the rice plant of claim 1 with a transgene that confers insect resistance.

9. An insect-resistant rice plant or rice seed produced by the method of claim 8.

10. A method of producing a disease-resistant rice plant, said method comprising transforming the rice plant of claim 1 with a transgene that confers disease resistance.

11. A disease-resistant rice plant or rice seed produced by the method of claim 10.

12. A method of producing a rice plant with modified fatty acid or modified carbohydrate metabolism, said method comprising transforming the rice plant of claim 1 with at least one transgene encoding a protein selected from the group consisting of fructosyltransferase, levansucrase, alpha-amylase, invertase, and starch-branching enzyme; or DNA encoding an antisense sequence to stearyl-ACP desaturase mRNA.

13. A rice plant or rice seed having modified fatty acid or modified carbohydrate metabolism, wherein said rice plant or rice seed is produced by the method of claim 12.

14. A method of producing a herbicide-tolerant rice plant, said method comprising transforming the rice plant of claim 1 with a gene that confers herbicide tolerance.

15. A herbicide-tolerant rice plant or rice seed produced by the method of claim 14.

16. A rice seed capable of producing the rice plant of claim 1, wherein said seed comprises at least one cell of the rice plant designated 'LAH169'.

* * * * *